US00PP29443P2

(12) United States Plant Patent
Grazzini

(10) Patent No.: US PP29,443 P2
(45) Date of Patent: Jul. 3, 2018

(54) ***LANTANA* PLANT NAMED 'DUELANHAVSUNRI'**

(50) Latin Name: *Lantana camara*
Varietal Denomination: Duelanhavsunri

(71) Applicant: Richard A. Grazzini, Bellefonte, PA (US)

(72) Inventor: Richard A. Grazzini, Bellefonte, PA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/731,082

(22) Filed: Apr. 15, 2017

(51) Int. Cl.
*A01H 5/02* (2018.01)

(52) U.S. Cl.
USPC ..... Plt./227
CPC ..... *A01H 5/02* (2013.01)

(58) Field of Classification Search
USPC ..... Plt./227
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Lantana* plant named 'Duelanhavsunri', characterized by its compact, upright and mounding plant habit; vigorous growth habit and rapid growth rate; freely branching growth habit; dense and bushy plant form; medium to large dark green-colored leaves; early and freely flowering habit; long flowering period; relatively large inflorescences with large flowers that are initially light yellow orange in color becoming light red purple with development; and good garden performance.

1 Drawing Sheet

Botanical designation: *Lantana camara.*
Cultivar denomination: 'DUELANHAVSUNRI'.

BACKGROUND OF THE INVENTION

The present invention relates to a new and distinct cultivar of *Lantana* plant, botanically known as *Lantana camara* and hereinafter referred to by the name 'Duelanhavsunri'.

The new *Lantana* plant is a product of a planned breeding program conducted by the Inventor in Bellefonte, Pa. The objective of the breeding program is to create new compact, freely-branching *Lantana* plants with early and freely flowering habit and large attractive flowers.

The new *Lantana* plant originated from a self-pollination in August, 2013 in Bellefonte, Pa. of a proprietary selection of *Lantana camara* identified as code number G2X-19104-1, not patented. The new *Lantana* plant was discovered and selected by the Inventor as a single flowering plant from within the progeny of the stated self-pollination in a controlled greenhouse environment in Bellefonte, Pa. on Oct. 8, 2014.

Asexual reproduction of the new *Lantana* plant by terminal cuttings in a controlled greenhouse environment in Bellefonte, Pa. since October, 2014 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duelanhavsunri'. These characteristics in combination distinguish 'Duelanhavsunri' as a new and distinct *Lantana* plant:

1. Compact, upright and mounding plant habit.
2. Vigorous growth habit and rapid growth rate.
3. Freely branching growth habit; dense and bushy plant form.
4. Medium to large dark green-colored leaves.
5. Early and freely flowering habit.
6. Long flowering period.
7. Relatively large inflorescences with large flowers that are initially light yellow orange in color becoming light red purple with development.
8. Good garden performance.

Plants of the new *Lantana* can be compared to plants of the parent selection. Plants of the new *Lantana* differ primarily from plants of the parent selection in the following characteristics:

1. Plants of the new *Lantana* are smaller and more compact than plants of the parent selection.
2. Plants of the new *Lantana* are not as vigorous as plants of the parent selection.
3. Plants of the new *Lantana* are more freely branching and denser than plants of the parent selection.
4. Leaves of plants of the new *Lantana* are darker green in color than leaves of plants of the parent selection.
5. Plants of the new *Lantana* and the parent selection differ in flower color as plants of the parent selection have flowers that are initially yellow in color becoming red purple in color with development.

Plants of the new *Lantana* can be compared to plants of the *Lantana camara* 'Bante Cheriasun', disclosed in U.S. Plant Pat. No. 19,264. In side-by-side comparisons, plants of the new *Lantana* differ from plants of 'Bante Cheriasun' in the following characteristics:

1. Plants of the new *Lantana* are larger and more vigorous than plants of 'Bante Cheriasun'.
2. Plants of the new *Lantana* flower earlier than plants of 'Bante Cheriasun'.
3. Plants of the new *Lantana* have slightly larger flowers than plants of 'Bante Cheriasun'.
4. Plants of the new *Lantana* and 'Bante Cheriasun' differ in flower color as developed flowers of plants of 'Bante Cheriasun' are darker red purple in color.

Plants of the new *Lantana* can be compared to plants of the *Lantana camara* 'Balandrise', disclosed in U.S. Plant Pat. No. 19,151. In side-by-side comparisons, plants of the new *Lantana* differ from plants of 'Balandrise' in the following characteristics:

1. Plants of the new *Lantana* are larger than plants of 'Balandrise'.
2. Plants of the new *Lantana* flower earlier than plants of 'Balandrise'.
3. Plants of the new *Lantana* have slightly larger flowers than plants of 'Balandrise'.
4. Plants of the new *Lantana* and 'Balandrise' differ in flower color as developed flowers of plants of 'Balandrise' are darker red purple in color.

BRIEF DESCRIPTION OF THE PHOTOGRAPH

The accompanying colored photograph illustrates the overall appearance of the new *Lantana* plant showing the colors as true as it is reasonably possible to obtain in colored reproductions of this type. Colors in the photograph may differ slightly from the color values cited in the detailed botanical description which accurately describe the colors of the new *Lantana* plant.

The photograph is a side perspective view of a typical flowering plant of 'Duelanhavsunri' grown in a container.

DETAILED BOTANICAL DESCRIPTION

The aforementioned photograph and following observations and measurements describe plants grown during the winter in one-gallon containers in a glass-covered greenhouse in Bellefonte, Pa. and under commercial practices typical of commercial *Lantana* production. During the production of the plants, day temperatures ranged from 15.5° C. to 24° C., night temperatures ranged from 12.8° C. to 21.1° C. and light levels ranged from 1 to more than 400 W/m$^2$. Plants were four months old when the photograph and the description were taken. In the following description, color references are made to The Royal Horticultural Society Colour Chart, Fifth Edition 2007, except where general terms of ordinary dictionary significance are used.

Botanical classification: *Lantana camara* 'Duelanhavsunri'.

Parentage:

*Female, or seed, parent*.—Proprietary selection of *Lantana camara* identified as code number G2X-19104-1, not patented.

*Male, or pollen, parent*.—Proprietary selection of *Lantana camara* identified as code number G2X-19104-1, not patented.

Propagation:

*Type*.—By terminal cuttings.

*Time to initiate roots, summer and winter*.—About 10 to 14 days at soil temperatures averaging 22.2° C. and ambient temperatures averaging 18.3° C.

*Time to produce a rooted young plant, summer and winter*.—About five to six weeks at soil temperatures averaging 22.2° C. and ambient temperatures averaging 18.3° C.

*Root description*.—Fibrous; medium in thickness.

*Rooting habit*.—Moderately freely branching; medium density.

Plant description:

*Plant and growth habit*.—Compact, upright and mounding plant habit; vigorous growth habit and rapid growth rate; freely branching growth habit; dense and bushy plant form.

*Plant height*.—About 46 cm to 58 cm.

*Plant diameter*.—About 46 cm to 58 cm.

Lateral branch description:

*Branching habit*.—Freely branching habit with about eight to ten primary lateral branches developing per plant; each primary lateral branch with potentially two secondary lateral branches developing at every node; pinching enhances lateral branch development, but is not required.

*Length*.—About 12 cm to 18 cm.

*Diameter*.—About 2 mm to 3 mm.

*Internode length*.—About 1.6 cm to 2 cm.

*Strength*.—Strong.

*Texture*.—Pubescent, scabrous; longitudinally ridged; becoming woody with development.

*Color, developing stems*.—Close to 144A.

*Color, developed stems*.—Close to 163A.

Leaf description:

*Arrangement*.—Opposite, simple.

*Length*.—About 6.6 cm to 7.4 cm.

*Width*.—About 4.4 cm to 6.4 cm.

*Shape*.—Ovate.

*Apex*.—Acute.

*Base*.—Attenuate.

*Margin*.—Serrate.

*Texture, upper and lower surfaces*.—Pubescent, scabrous; moderately rugose.

*Venation pattern*.—Pinnate.

*Color*.—Developing and fully expanded leaves, upper surface: Close to N137A; venation, close to N137A. Developing and fully expanded leaves, lower surface: Close to 138A; venation, close to 138A.

*Petiole length*.—About 1.5 cm.

*Petiole diameter*.—About 2.5 mm.

*Petiole texture, upper and lower surfaces*.—Pubescent, scabrous.

*Petiole color, upper and lower surfaces*.—Close to 138A.

Flower description:

*Flower arrangement and flowering habit*.—Solitary salverform flowers arranged in terminal and axillary hemispherical umbels; flowers face mostly upward or outward; freely flowering habit with about 25 to 35 flowers developing per inflorescence and numerous inflorescences developing per plant during the flowering season.

*Natural flowering season*.—Early flowering habit, plants begin flowering about 13 to 14 weeks from unrooted cuttings; long flowering period, plants of the new *Lantana* flower continuously throughout the summer in the northern United States.

*Flower longevity on the plant*.—About four weeks; flowers not persistent.

*Fragrance*.—Fragrant; spicy, slightly fetid.

*Inflorescence height*.—About 2 cm to 2.3 cm.

*Inflorescence diameter*.—About 4.2 cm to 4.7 cm.

*Flowers*.—Appearance: Flared trumpet, corolla fused, five-parted; flowers are sessile. Diameter: About 9 mm to 10 mm. Depth (height): About 2.1 cm.

*Flower buds*.—Length: About 7 mm. Diameter: About 3 mm. Shape: Tubular. Color: Close to 144C.

*Corolla*.—Arrangement: Single whorl of five fused petals. Petal lobe length: About 6 mm to 7 mm. Petal lobe width: About 6 mm to 8 mm. Petal lobe shape: Obovate. Petal lobe apex: Acute. Petal margin: Entire. Petal texture, upper and lower surfaces: Papillose. Color: When opening, upper surface: Close to 10C suffused with close to 27B. When opening, lower surface: Close to 27B. Fully opened, upper surface: Close to 65B; towards the throat, close to 10C; color does not change with development. Fully opened, lower surface: Close to 69A; color does not change with development. Throat: Close to 10C. Tube: Close to 69A.

*Calyx*.—Appearance: Tubular calyx with five fused sepals. Length: About 5 mm to 7 mm. Diameter: About 2 mm. Sepal shape: Lanceolate. Sepal apex: Acute. Sepal margin: Entire. Sepal texture, inner and outer surfaces: Pubescent. Sepal color, upper surface: Close to 144B. Sepal color, lower surface: Close to 144C.

*Peduncles*.—Length: About 1.9 cm to 2.2 cm. Diameter: About 1 mm to 1.5 mm. Strength: Strong. Texture: Pubescent. Color: Close to 144A.

*Reproductive organs*.—Stamens: Quantity and arrangement: Four per flower, adnate to floral tube. Filament length: About 0.5 mm. Filament color: Close to 4C. Anther length: About 1 mm. Anther shape: Oblong, bi-lobed. Anther color: Close to 9A. Pollen amount: Sparse. Pollen color: Close to 4B. Pistils: Quantity: One per flower. Pistil length: About 3 mm to 4 mm. Stigma color: Close to 145A. Style length: About 2.5 mm to 3 mm. Style color: Close to 155C. Fruits and seeds: Fruit and seed development have not been observed on plants of the new *Lantana* to date.

Garden performance: Plants of the new *Lantana* have been observed to have good garden performance and to tolerate wind, rain and temperatures ranging from about 13° C. to about 38° C.

Pathogen & pest tolerance: Plants of the new *Lantana* have not been observed to be tolerant to pathogens and pests common to *Lantana* plants to date.

It is claimed:

1. A new and distinct *Lantana* plant named 'Duelanhavsunri' as illustrated and described.

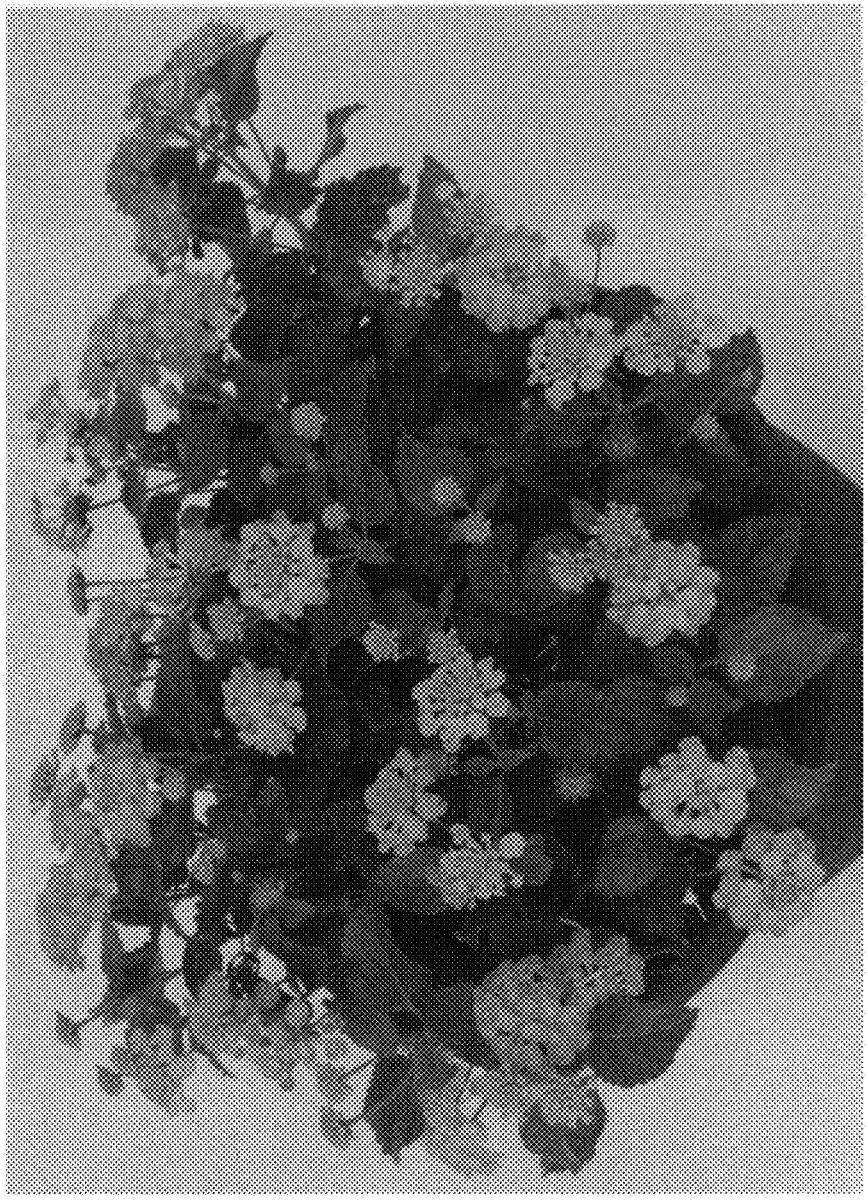

* * * * *